(12) United States Patent
Guntoori et al.

(10) Patent No.: US 6,586,593 B1
(45) Date of Patent: Jul. 1, 2003

(54) EFFICIENT PROCESS FOR THE PREPARATION OF LAMOTRIGINE AND RELATED 3,5-DIAMINO-6-SUBSTITUTED-1,2,4-TRIAZINES

(75) Inventors: Bhaskar Reddy Guntoori, Brantford (CA); Daqing Che, Brantford (CA); K. S. Keshava Murthy, Brantford (CA)

(73) Assignee: Brantford Chemicals Inc., Brantford (CA)

( * ) Notice: Subject to any disclaimer, the term of this patent is extended or adjusted under 35 U.S.C. 154(b) by 0 days.

(21) Appl. No.: 10/046,383

(22) Filed: Jan. 16, 2002

(30) Foreign Application Priority Data

Dec. 24, 2001 (CA) .............................. 2366521

(51) Int. Cl.⁷ ......................................... C07D 253/075
(52) U.S. Cl. ...................................... 544/182
(58) Field of Search ......................... 544/182

(56) References Cited

U.S. PATENT DOCUMENTS

| 4,602,017 A | 7/1986 | Sawyer et al. ............... 514/242 |
| 6,329,521 B2 * | 12/2001 | Nadaka et al. ............... 544/182 |

FOREIGN PATENT DOCUMENTS

| CA | 1112643 | 11/1981 |
| CA | 1133938 | 10/1982 |
| EP | 963980 | 12/1999 |
| GB | 759014 | 10/1956 |
| WO | WO 96/20934 | 11/1996 |
| WO | WO 96/20935 | 11/1996 |
| WO | WO 00/35888 | 6/2000 |

\* cited by examiner

*Primary Examiner*—Venkataraman Balasubramanian
*Assistant Examiner*—C. Styles
(74) *Attorney, Agent, or Firm*—Marcelo K. Sarkis; Kitt Sinden; Ivor M. Hughes

(57) ABSTRACT

A process for the manufacture of 3,5-diamino-6-substituted-1,2,4-triazines is disclosed which comprises the steps of:

(a) reacting a compound of formula (II):

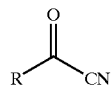

formula II with aminoguanidine salts, (b) dehydrating the compound obtained to form a compound of formula IV,

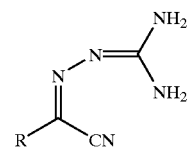

formula IV and (c) cyclization of the compound of formula IV into a 3,5-diamino-6-substituted-1,2,4-triazine compound of formula I or into a hydrated form thereof.

26 Claims, 6 Drawing Sheets

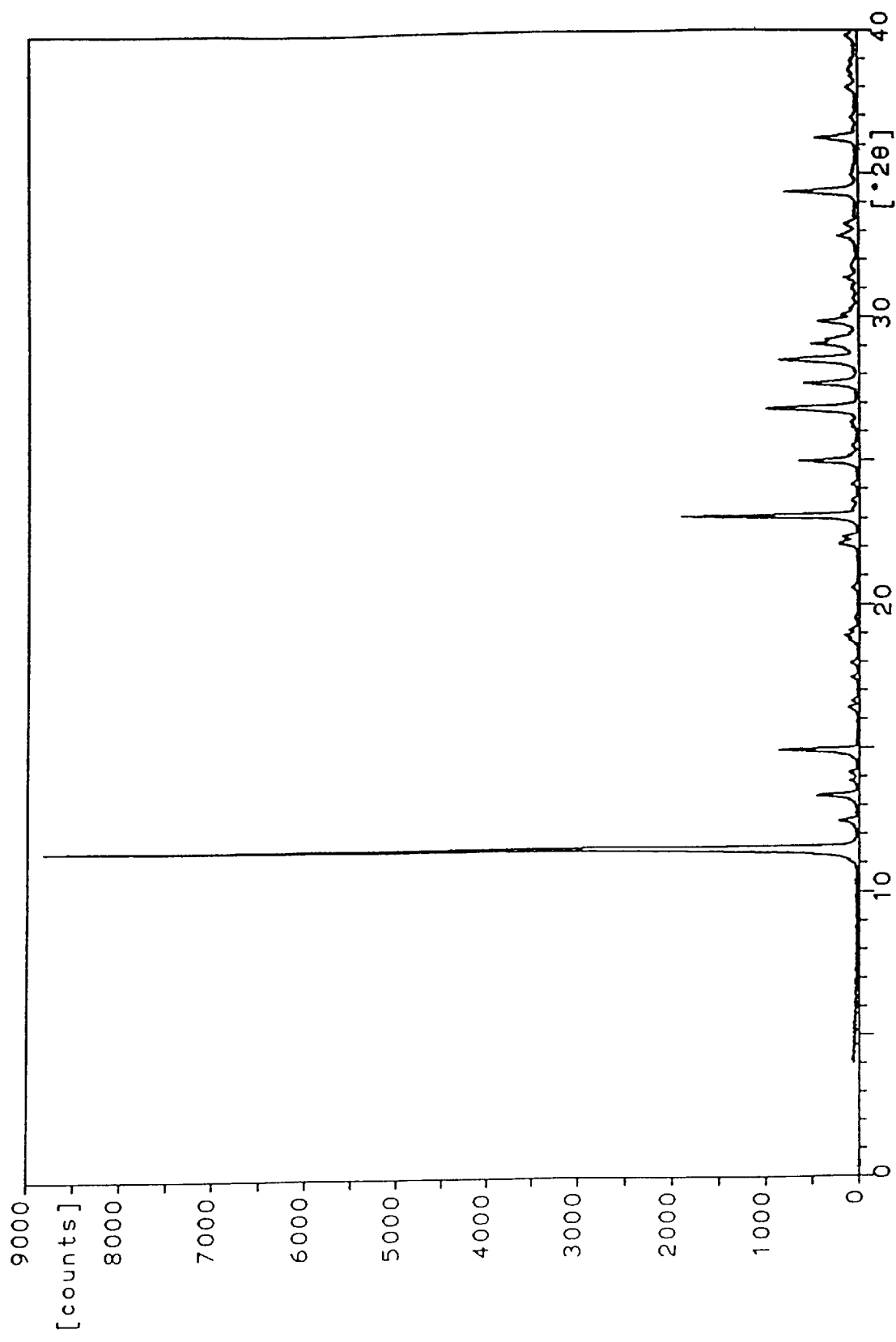
FIG. 1: Powder X-ray diffraction pattern analysis of lamotrigine monohydrate

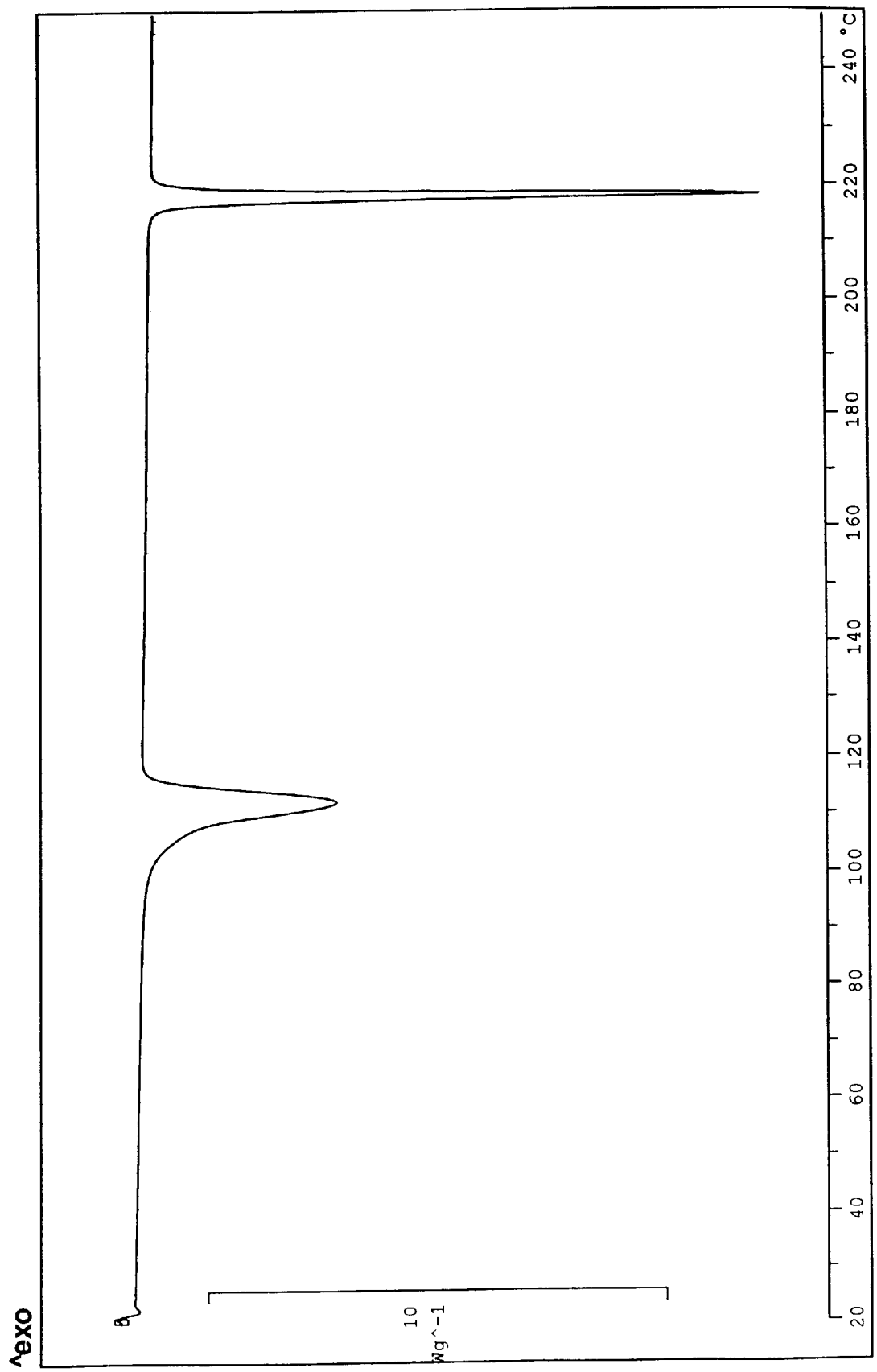
FIG. 2: Differential scanning calorimetry thermogram (DSC) of lamotrigine monohydrate

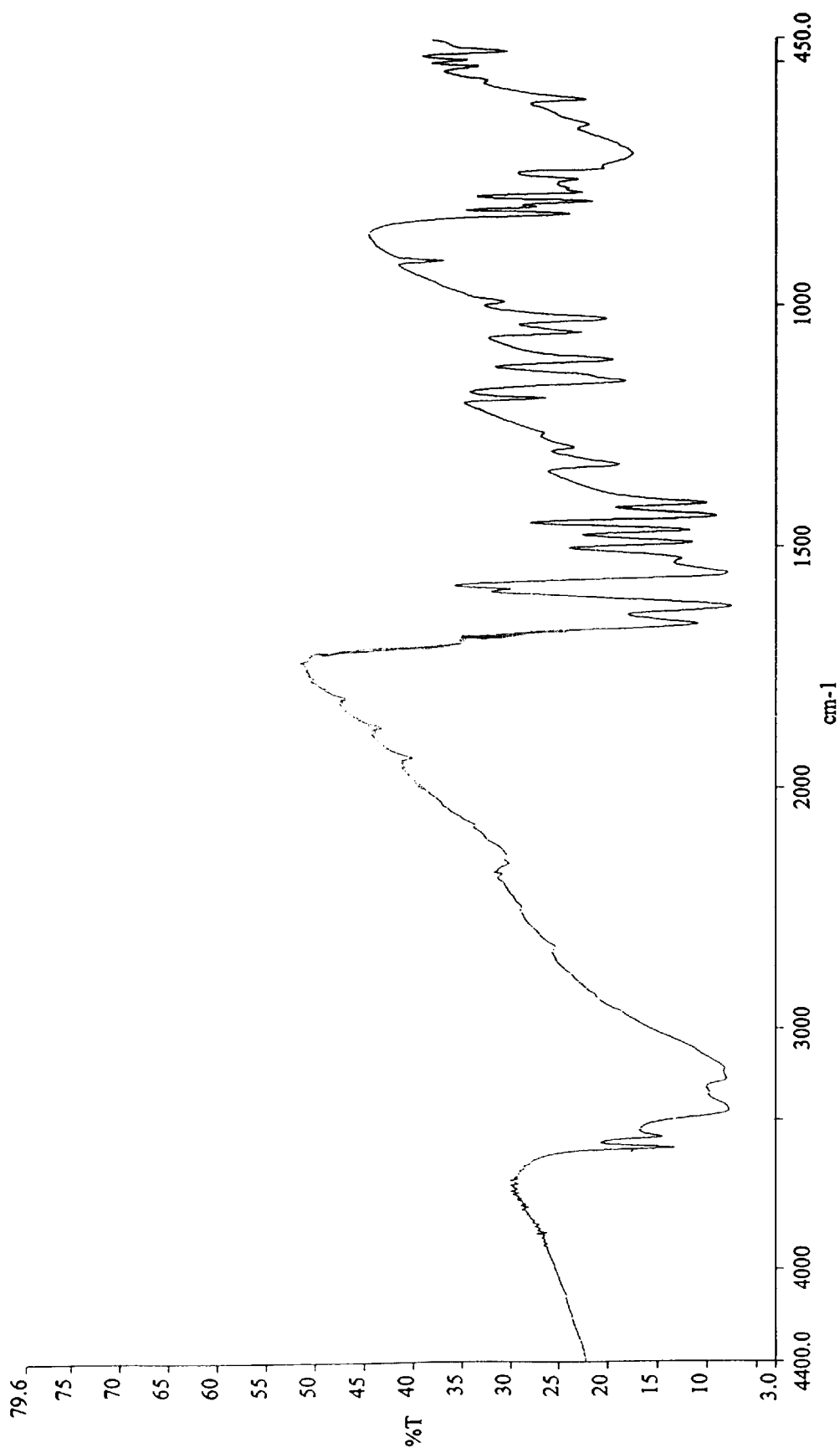
FIG. 3: Fourier transform infrared spectrum (FTIR) of lamotrigine monohydrate

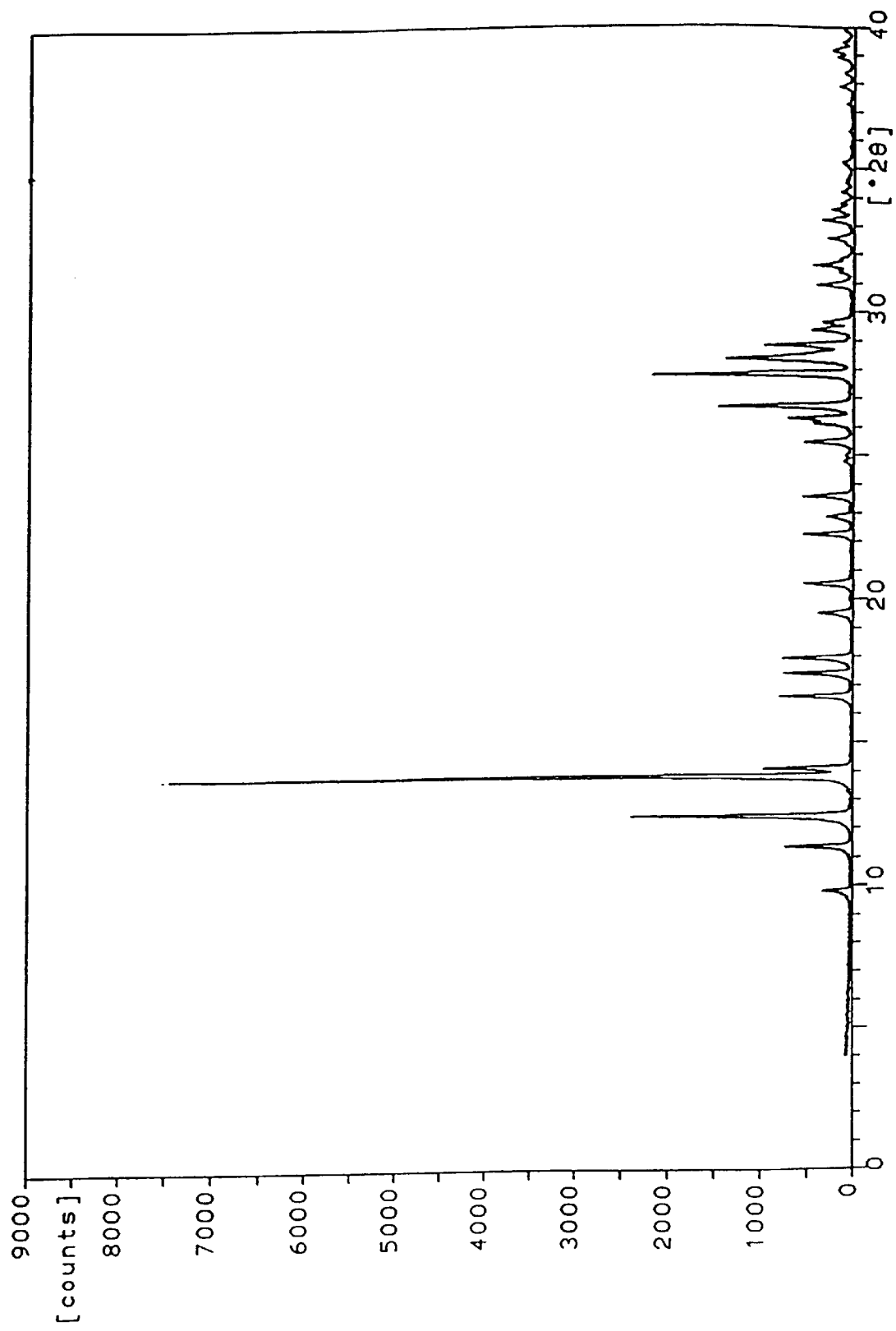
FIG. 4: Powder X-ray diffraction pattern analysis of anhydrous lamotrigine

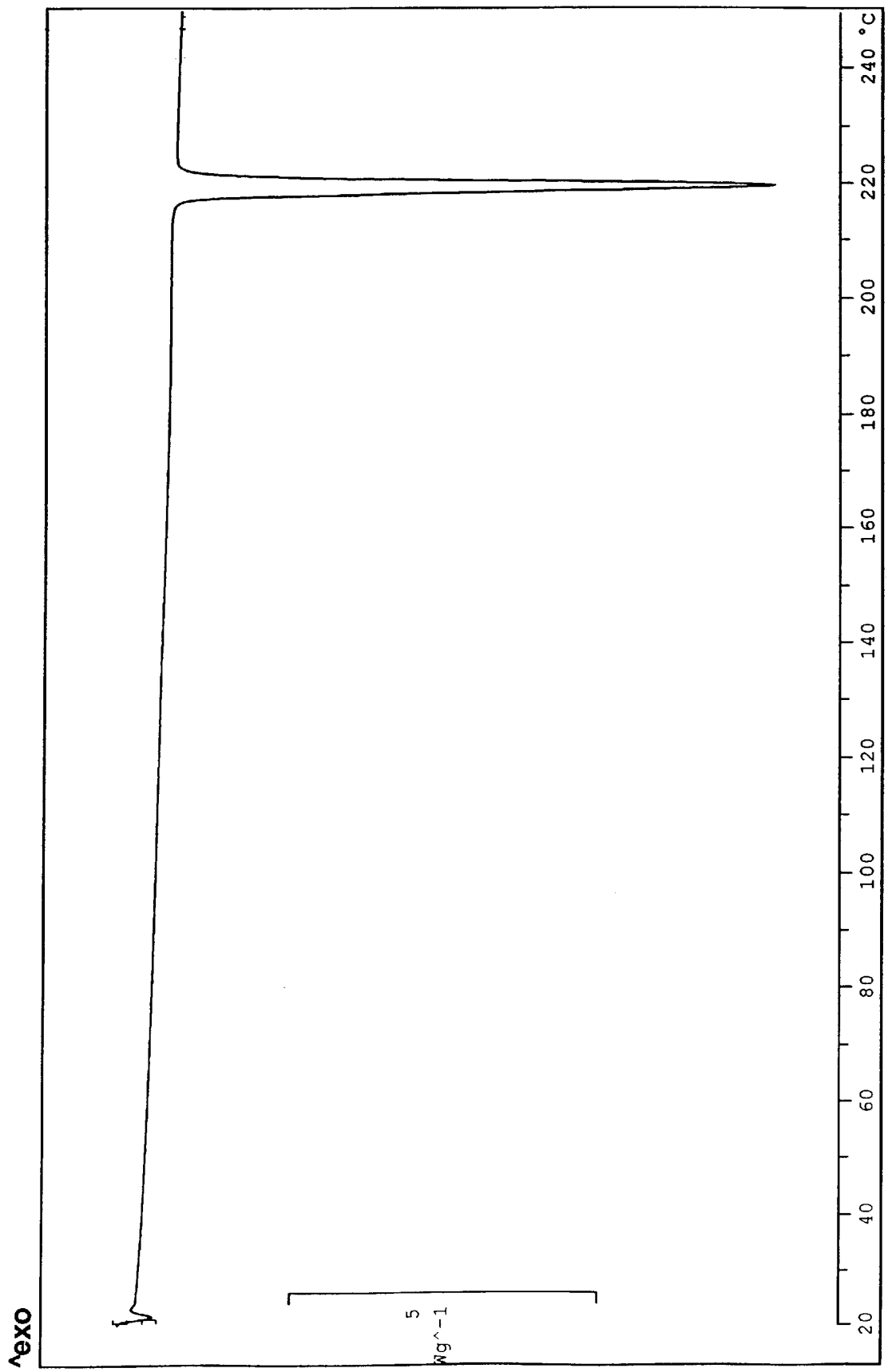
FIG. 5: Differential scanning calorimetry thermogram (DSC) of anhydrous lamotrigine

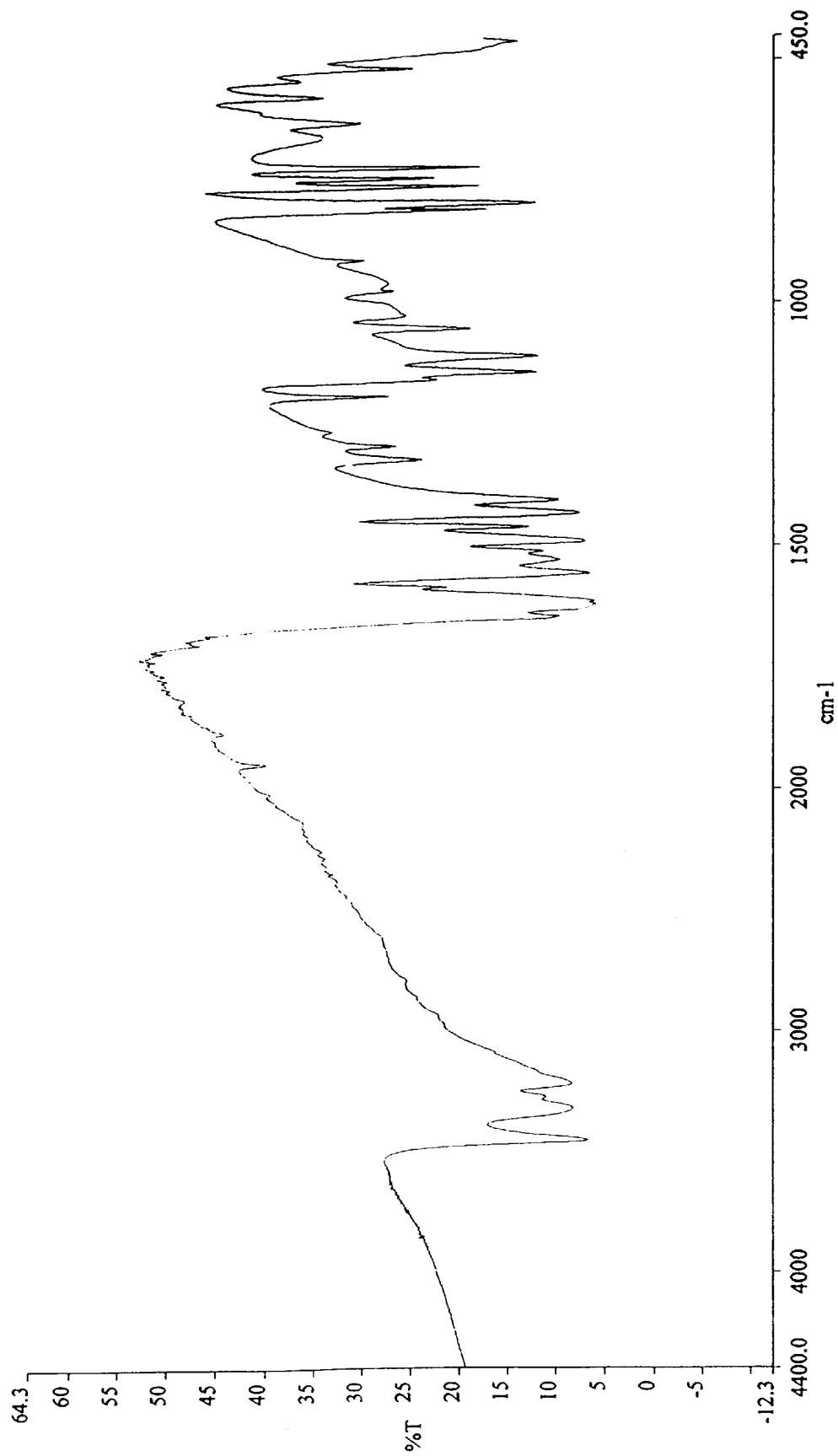
FIG. 6: Fourier transform infrared spectrum (FTIR) of anhydrous lamotrigine

EFFICIENT PROCESS FOR THE PREPARATION OF LAMOTRIGINE AND RELATED 3,5-DIAMINO-6-SUBSTITUTED-1,2,4-TRIAZINES

FIELD OF THE INVENTION

The present invention relates to novel processes for the production of 3,5-diamino-6-substituted-1,2,4-triazines in general, and the antiepileptic agent Lamotrigine in particular.

BACKGROUND OF THE INVENTION

Lamotrigine 1, 3,5-diamino-6-(2,3-dichlorophenyl)-1,2,4-triazine, is an antiepileptic drug, and its analogues were first disclosed in British Patent No. 759,014 (1956). Subsequently, Lamotrigine and its analogues were described in Canadian Patent Nos. 1,112,643 and 1,133,938, and in U.S. Pat. No. 4,602,017. Processes for the preparation of Lamotrigine are also disclosed in international publications and patents WO 96/20934, WO 96/20935, WO 00/35888 and European Patent No. 963,980.

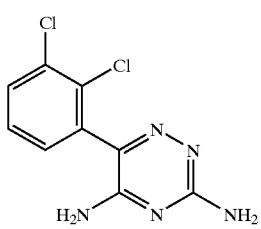

Lamotrigine 1

The process (as disclosed in Canadian Patent Nos. 1,112,643 and 1,133,938, U.S. Pat. No. 4,602,017 and in British Patent No. 759,014) for the preparation of Lamotrigine involves reaction of 2,3-dichlorobenzoyl cyanide 2 and aminoguanidine bicarbonate in dimethylsulfoxide and 8N aqueous nitric acid (scheme 1). The above process uses drastic conditions (20 eq. 8N $HNO_3$), excess reagents and requires 7 days for completion of the reaction. The overall yield of the process from 2,3-dichlorobenzoyl cyanide is 15.6%.

Scheme 1

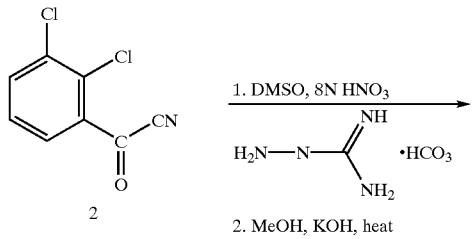

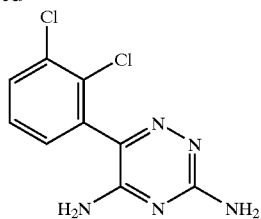

Lamotrigine 1
15.6% yield

The process reported in WO 00/35888 for this reaction uses $H_2SO_4$ instead of 8N $HNO_3$. However, it also suffers from lower yield (40%) and longer reaction time (2.5 days). The process also uses a large excess (~11 times) of sulfuric acid.

It is accordingly an object of the present invention to provide an improved process for the manufacture of lamotrigine which overcome the problems associated with poor efficiency described in the prior art. More broadly, it is an object of the present invention to provide novel processes for the production of 3,5-diamino-6-substituted-1,2,4-triazines.

SUMMARY OF THE INVENTION

In accordance with one aspect of the present invention, there is provided a process for the manufacture of an intermediate compound of formula IV

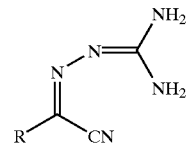

formula IV useful for manufacturing 3,5-diamino-6-substituted-1,2,4-triazines, wherein R is an optionally substituted $C_1$–$C_4$ alkyl or aryl group, which process comprises reacting a compound of formula II:

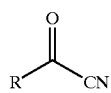

formula II with aminoguanidine in the presence of an acid in an organic solvent under anhydrous conditions followed by treatment with a dehydrating reagent.

In accordance with another aspect of the present invention there is provided a process for the manufacture of 3,5-diamino-6-substituted-1,2,4-triazines of formula I:

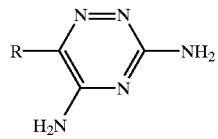

formula I comprising the steps of:

(a) reacting a compound of formula (II):

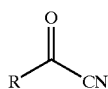

formula II with aminoguanidine salts, or equivalent thereof, in the presence of an acid in an organic solvent under anhydrous conditions to form a cyanohydrin of formula III:

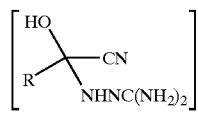

formula III (b) dehydrating the cyanohydrin of formula III to form a compound of formula IV by treatment with a dehydrating reagent,

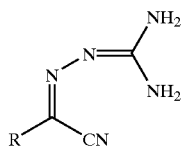

formula IV and (c) cyclization of the compound of formula IV into a 3,5-diamino-6-substituted-1,2,4-triazine of compound of formula I or into a hydrated form thereof.

Suitably the substituted $C_1$–$C_4$ alkyl group is methyl, ethyl, propyl or butyl and the substituted aryl group is preferably 2,3-dichlorophenyl.

The process of the present invention provides a high yielding and cost-effective process for the preparation of 3,5-diamino-6-substituted-1,2,4-triazines in general and Lamotrigine in particular. This result is obtained through the use of an additive, namely a dehydrating agent, such as thionyl chloride, $POCl_3$ or $PCl_5$, and by employing organic acid in combination with a polar organic solvent, which stabilizes the cyanohydrin of formula III. The cyanohydrin of formula III upon addition of a dehydrating agent affords the intermediate iminoguanidine of formula IV (scheme 2).

The acid used in this process can be dry organosulfonic acids such as methanesulfonic acid or para-toluenesulfonic acid, either in combination with dry polar organic solvents, such as dimethylformamide (DMF), N-methyl-2-pyrrolidinone (NMP) or dimethylsulfoxide (DMSO), or combinations of a polar solvent with nonpolar solvents such as tetrahydrofuran (THF). The dehydrating reagents used in the process can be $SOCl_2$, $POCl_3$ or $PCl_5$, oxalyl chloride, phosgene or equivalents thereof.

Scheme 2

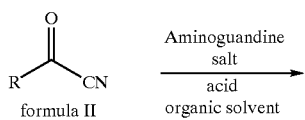

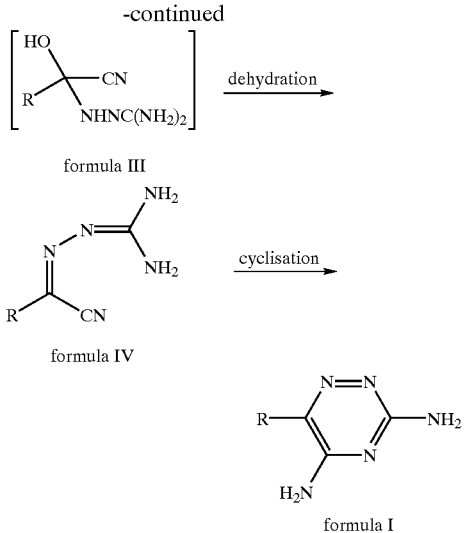

The process, as shown in Scheme 2, involves the reaction of aryl cyanide, preferably 2,3-dichlorobenzoyl cyanide 2 (in which R=2,3-dichlorophenyl), with an organic acid, for example para-toluenesulfonic acid or methanesulfonic acid, and dry organic solvents, for example DMSO, NMP or DMF, at suitable temperatures to form an intermediate of formula III. The reaction mixture is treated with dehydrates for example $SOCl_2$, $POCl_3$ or $PCl_5$, oxalyl chloride, phosgene or equivalent thereof at a suitable temperature to form the iminoguanidine of formula IV. The iminoguanidine salt in the reaction mixture is cyclized upon basification and heating. The iminoguanidine salt can be basified and isolated by filtration. The isolated iminoguanidine can be cyclized to form Lamotrigine using a base (such as NaOH, $NH_3$ or KOH) in a protic solvent (such as methanol, ethanol, isopropanol or water). Lamotrigine 1 can be isolated as the monohydrate when the cyclization of the intermediate is carried out using base and isopropanol/water mixture or NMP/water. The lamotrigine monohydrate is a new compound and is further characterized in having the following peaks in powder X-ray diffraction pattern at an angle of two theta (2θ) is found to be: 10.34, 11.53, 12.46, 13.36, 13.86, 14.15, 14.94, 16.43, 16.65, 17.44, 17.97, 18.77, 18.91, 19.11, 19.52, 20.58, 22.11, 22.31, 23.09, 23.61, 24.18, 24.99, 25.52, 26.31, 26.83, 27.68, 28.53, 29.07, 29.24, 29.86, 30.09, 30.63, 31.01, 31.37, 31.78, 32.82, 33.25, 34.35, 34.96, 36.23, 36.92, 37.97, 38.60, 38.90. The positions of the peaks in powder X-ray diffraction pattern studies of anhydrous lamotrigine at an angle of two theta (2θ) to be 9.80, 11.39, 12,46, 13.29, 13.86, 14.13, 15.62, 16.66, 17.44, 17.97, 19.54, 20.56, 22.30, 22.89, 23.61, 24.81, 25.50, 26.31, 26.74, 27.87, 28.42, 28.86, 29.38, 29.66, 30.95, 31.66, 32.59, 33.23, 33.61, 33.83, 34.21, 35.20, 36.27, 37.16, 37.90, 38.35, 38.92, 39.17, 39.45.

The overall yield of lamotrigine is high (molar yield: 80–85%). The above described process is very cost-effective, operationally simple and completed in a short time period (6 to 10 hours).

BRIEF DESCRIPTION OF THE DRAWINGS

FIG. 1 is the powder X-ray diffraction pattern of lamotrigine monohydrate.

FIG. 2 is a differential scanning calorimetry thermogram (DSC) of lamotrigine monohydrate.

FIG. 3 is a Fourier transform infrared spectrum (FTIR) of lamotrigine monohydrate.

FIG. 4 is the powder X-ray diffraction pattern of anhydrous lamotrigine.

FIG. 5 is a differential scanning calorimetry thermogram (DSC) of anhydrous lamotrigine.

FIG. 6 is a Fourier transform infrared spectrum (FTIR) of anhydrous lamotrigine.

The following examples serve to illustrate embodiments of the present invention in a manner in which they can be practiced but, as such, should not be considered in a limiting sense.

EXAMPLES

Procedure I

To a round bottomed flask was added aminoguanidine hydrochloride (116.1 g, 1.05 mol) and dimethylformamide (900 mL). To this mixture was added methanesulfonic acid (130.4 g, 1.36 mol) followed by adding 2,3-dichlorobenzoylcyanide (150.0 g, 0.75 mol). The reaction mixture was stirred for 1 hour and then the dehydrating reagent, thionyl chloride, (45.2 g, 0.38 mol) was added. The reaction mixture was stirred for another hour and then basified with KOH solution (4N). The precipitate was filtered and washed with water.

Yield: 401.3 g damp cake (KF=39.2%).

Analytically pure sample of the intermediate is prepared as following:

20.0 g of the damp cake was suspended in 60 ml MeOH and stirred at room temperature for 3 hours. The solid was filtered and dried in vacuum at room temperature to give 5.4 g analytic pure iminoguanidine as a yellow solid.

m.p.: 179~180° C. (corrected). MS (m/z): 256.3 [M$^+$] IR: 3491.8; 3457.1 (Amine N-H stretching); 2207.5 (CN stretching); 1681.9 (Imine C=N stretching); 1055.5 ($C_{aryl}$-Cl stretching). $^1$H-NMR (300 MHz, DMSO-D6): 7.66 (ad, J 7.9 Hz, 2H), 7.41 (dd, J=7.9; 7.9 Hz, 1H), 6.70 (br s, NH$_2$). $^{13}$C-NMR (75 MHz, DMSO-D6): 163.6, 135.3, 132.4, 130.0, 129.5, 129.0, 128.2, 114.4, 113.8.

| Elemental analysis: | C | H | N |
|---|---|---|---|
| Calculated: | 42.21 | 2.76 | 27.35 |
| Found: | 42.10 | 2.49 | 27.69 |

Procedure II

A round bottomed flask was charged with iminoguanidine (401.3 g from procedure I), isopropanol (1000.0 ml) and KOH (85%, 12.0 g, 0.18 mol). The reaction mixture was refluxed for 3 hours. Isopropanol was distilled and water (800 ml) was added. The reaction mixture was stirred for 3 hours, the solid was filtered and washed with water. The damp cake is dried under vacuum to yield 168.5 grams of lamotrigine monohydrate as crystalline solid (82% based on 2,3-dichlorobenzoyl cyanide).

Procedure III (Without Isolation of Intermediate of Formula IV)

To a round bottomed flask was added aminoguanidine hydrochloride (116.1 g, 1.05 mol) and dimethylformamide (900 ml). To this mixture was added methanesulfonic acid (130.4 g, 1.36 mol) followed by 2,3-dichlorobenzoyl cyanide (150.0 g, 0.75 mol). The reaction mixture was stirred for 1 hour and then dehydrating reagent thionyl chloride (45.2 g, 0.38 mol) was added slowly. The reaction mixture was stirred for another hour and then basified with KOH solution (4 N). The Reaction mixture was heated under reflux (100~105° C.) for 3~4 hours and cooled slowly to room temperature. The solid was filtered and washed with water. After drying, 160.7 g of lamotrigine monohydrate as a crystalline solid (78% based on 2,3-dichlorobenzoyl cyanide) was obtained.

See also FIGS. 1, 2, 3.

Karl Fischer (water content): 5.92~6.03%

DSC: 106.86, 216.650° C. (onset). MS (m/z): 256.3 [M$^+$] IR: 3496.9; 3450.3; 3338.5; 3211.0; 1658.7; 1524.0; 1328.8; 1027.1. $^1$H-NMR (300 MHz, DMSO-D6): 7.66 (ad, J=7.9 Hz, 2H), 7.41 (dd, J=7.9; 7.9 Hz, 1H), 6.70 (br s, NH$_2$). $^{13}$C-NMR (75 MHz, DMSO-D6): 163.6, 135.3, 132.4, 130.0, 129.5, 129.0, 128.2, 114.4, 113.8.

Procedure IV (Preparation of Anhydrous Lamotrigine from Lamotrigine Monohydrate)

150 g lamotrigine monohydrate (from procedure II or III) was recrystallized in 900 mL isopropanol giving 132 g (94%) of anhydrous lamotrigine as a crystalline solid.

See also FIGS. 4, 5, 6.

m.p.: 216~217° C. (corrected). MS (m/z): 256.3 [M$^+$] $^1$H-NMR (300 MHz, DMSO-D6): 7.69 (dd, J=1.7; 7.9 Hz, 1H), 7.43 (dd, J=7.9; 7.6 Hz, 1H), 7.35 (dd, J=1.7; 7.6 Hz, 1H), 6.70 (br s, NH$_2$), 6.44 (br s, NH$_2$). $^{13}$C-NMR (75 MHz, DMSO-D6): 162.1, 154.1, 138.3, 136.8, 132.0, 131.6, 130.6, 128.5.

| Elemental analysis: | C | H | N |
|---|---|---|---|
| Calculated: | 42.21 | 2.76 | 27.35 |
| Found: | 42.10 | 2.58 | 27.46 |

The embodiments of the invention in which an exclusive property or privilege is claimed are as following:

1. A process for the manufacture of 3,5-diamino-6-substituted-1,2,4-triazines of formula (I):

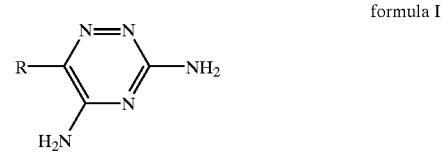

formula I wherein R is optionally substituted $C_1$–$C_4$ alkyl or aryl group, the process comprising the steps of:
(a) reacting a compound of formula (II):

formula II wherein R is optionally substituted $C_1$–$C_4$ alkyl or aryl group,
with aminoguanidine in the presence of an organic sulphonic acid in an organic solvent under anhydrous conditions to form a cyanohydrin of formula III:

formula III wherein R is optionally substituted $C_1$–$C_4$ alkyl or aryl group, (b) dehydrating the cyanohydrin of formula III to form a compound of formula IV by using a dehydrating reagent,

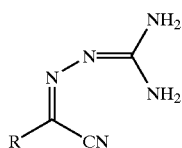

formula IV wherein R is optionally substituted $C_1$–$C_4$ alkyl or aryl group,
and
(c) cyclization of the compound of formula IV into a 3,5-diamino-6-substituted-1,2,4-triazine compound of formula I or into a hydrated form thereof.

2. The process of claim 1 wherein the aryl group is 2,3-dichlorophenyl.

3. The process of claim 1 wherein the 3,5-diamino-6-substituted-1,2,4-triazine produced is 3,5-diamino-6-(2,3-dichlorophenyl)-1,2,4-triazine.

4. The process of claim 1 wherein the hydrated form is 3,5-diamino-6-(2,3-dichlorophenyl)-1,2,4-triazine monohydrate.

5. The process of claim 1, 2, 3 or 4 wherein said organic solvent is selected from the group consisting of DMF, NMP, and DMSO and mixtures thereof.

6. The process of claim 1, 2, 3 or 4 wherein said organic sulphonic acid is selected from the group consisting of methanesulphonic acid and para-toluenesulfonic acid.

7. The process of claim 1, 2, 3 or 4 wherein the dehydrating reagent is selected from the group consisting of $SOCl_2$, $POCl_3$, $(COCl)_2$, $PCl_5$ and phosgene.

8. The process of claim 6 wherein the dehydrating reagent is $SOCl_2$.

9. The process of claim 6 wherein the dehydrating reagent is $POCl_3$.

10. The process of claim 6 wherein the dehydrating reagent is $(COCl)_2$.

11. The process of claim 6 wherein the dehydrating reagent is $PCl_5$.

12. The process of claim 6 wherein the dehydrating reagent is phosgene.

13. The process of claim 6 wherein the organic solvent is selected from the group consisting of DMF, NMP and DMSO and mixtures thereof.

14. The process of claim 13 wherein said organic solvent is mixed with a non-polar solvent.

15. A process for the manufacture of compound of formula (IV):

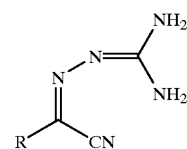

formula IV wherein R is optionally substituted $C_1$–$C_4$ alkyl or aryl group, the process comprising:
reacting compound of formula (II):

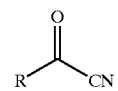

formula II wherein R is optionally substituted $C_1$–$C_4$ alkyl or aryl group,
with aminoguanidine in the presence of an organic sulphonic acid in an organic solvent under anhydrous conditions followed by treatment with a dehydrating reagent.

16. The process of claim 15 wherein the aryl group is 2,3-dichlorophenyl.

17. The process of claim 15 or 16 wherein said organic sulphonic acid is selected from the group consisting of methanesulfonic acid and para-toluenesulfonic acid.

18. The process of claim 17 wherein said organic solvent is mixed with a non-polar solvent.

19. The process of claim 15 or 16 wherein the dehydrating reagent is selected from the group consisting of $SOCl_2$, $POCl_3$, $(COCl)_2$, $PCl_5$, and phosgene.

20. The process of claim 17 wherein the dehydrating reagent is $SOCl_2$.

21. The process of claim 17 wherein the dehydrating reagent is $POCl_3$.

22. The process of claim 17 wherein the dehydrating reagent is $(COCl)_2$.

23. The process of claim 17 wherein the dehydrating reagent is $PCl_5$.

24. The process of claim 17 wherein the dehydrating reagent is phosgene.

25. The process of claim 19 wherein the organic solvent is selected from the group consisting of DMF, NMP and DMSO and mixtures thereof.

26. The process of claim 18 wherein said organic solvent is selected from the group consisting of DMF, NMP and DMSO and mixtures thereof.

\* \* \* \* \*